United States Patent [19]

Uemura et al.

[11] 4,340,589
[45] Jul. 20, 1982

[54] ANTITHROMBIN PREPARATION AND PROCESS FOR THE PRODUCTION THEREOF

[75] Inventors: Yahiro Uemura, Hirakata; Midori Nagatomo, Takatsuki; Satoshi Funakoshi, Katano; Tadakazu Suyama, Kyoto, all of Japan

[73] Assignee: The Green Cross Corporation, Osaka, Japan

[21] Appl. No.: 237,125

[22] PCT Filed: Jun. 18, 1979

[86] PCT No.: PCT/JP79/00154

§ 371 Date: Feb. 18, 1981

§ 102(e) Date: Feb. 17, 1981

[87] PCT Pub. No.: WO80/02798

PCT Pub. Date: Dec. 24, 1980

[51] Int. Cl.$^3$ ............................................. A61K 35/14
[52] U.S. Cl. ................................. 424/101; 260/112 R

[58] Field of Search ...................... 424/101; 260/112 R

[56] References Cited

U.S. PATENT DOCUMENTS 3,842,061 10/1974 Andersson et al. ................. 424/101
4,087,415 5/1978 Bick et al. ........................... 424/101

OTHER PUBLICATIONS

Wilson et al., Chem. Abst. vol. 88, (1978), p. 110,515w.

*Primary Examiner*—Sam Rosen
*Attorney, Agent, or Firm*—Cushman, Darby & Cushman

[57] ABSTRACT

An antithrombin preparation, secure and stable for a long period of time, can be obtained by freeze-drying an aqueous solution containing antithrombin-III as main component in the presence of an effective quantity of at least one member selected from the group consisting of proteins, sugars, amino acids, inorganic salts and salts of organic acids as stabilizer.

15 Claims, No Drawings

ANTITHROMBIN PREPARATION AND PROCESS FOR THE PRODUCTION THEREOF

TECHNICAL FIELD

This invention relates to a dry antithrombin preparation containing antithrombin-III of human origin as a main ingredient, as well as to a process for its production.

BACKGROUND ART

It is well known that thrombin having a blood coagulant action acts upon fibrin to produce a fibrin monomer, the fibrin monomer polymerizes to form a network of fibrin fiber and, at the same time, the network takes blood corpuscles into itself to yield a thrombus with which bleedings are stopped.

Although thrombin usually exists in living body as inactive prothrombin, it can sometimes be activated little by little to give thrombin. However, the thrombin is neutralized by antithrombins which simultaneously exist in the living body, so that coagulation of blood does not take place immediately.

In cases of disseminated intravascular coagulation (DIC) and fibrinopenia, the activation of prothrombin in living body is abnormally accelerated and surpasses the neutralizing action of antithrombins, followed by the occurence of coagulation of blood and forms thrombin in various localities of living body.

Accordingly, abnormalities such as DIC can be remedied by reinforcing the antithrombin action. Substances having in vivo antithrombin activity include antithrombin-III, fibrin and its decomposition products, $\alpha_2$-macroglobulin and the like, among which antithrombin-III has the strongest activity so that production of a stable preparation therefrom is awaited.

Antithrombin-III herein referred to is a substance having an ability to inactivate human thrombin. It can be recovered from whole blood, plasma or serum of human. A serum expressed out of coagulated blood contains this substance, which cannot coagulate purified fibrinogen.

As the methods for purifying antithrombin-III, aluminum hydroxide adsorption method, DEAE-cellulose ion-exchange chromatography method and heparin-Sephalose adsorption method (Japanese Patent Kokai (Laid-Open) No. 35017/1973, U.S. Pat. No. 3,842,061) can be referred to. Though antithrombin-III obtained by these methods is relatively stable in a liquid state, the loss of antithrombin-III is rather significant at the time of freezing or freeze-drying which are generally considered most effective for the long term stabilization of proteins and the like.

Since antithrombin-III has some stability in liquid state, it may be possible to produce a liquid preparation of antithrombin-III. However, liquid preparation is undesirable because of the fault that activity of liquid preparation decreases after a long period of storage and deposition of insoluble matter can occur in some lots.

Although several processes for purifying antithrombin-III have already been reported as above, the process for producing a medical preparation therefrom is not yet accomplished, which is due to the fact that no technique has been developed for stabilizing the purified product for a long period of time.

The present inventors conducted a continuous study on the process for making antithrombin-III into a preparation and the method for stabilizing antithrombin-III during freeze-drying. As the result, the inventors succeeded in discovering a stabilizer useful for the purpose and developing an antithrombin preparation containing a freeze-dried antithrombin-III as a main ingredient in a form secure and stabilized for a long period of time. Based on this success, this invention was accomplished.

It is an object of this invention to provide a dry antithrombin preparation containing antithrombin-III as a main ingredient which is secure, stable for a long period of time, as well as to process for its production.

DISCLOSURE OF INVENTION

Other objects and advantages of this invention be apparent from the description given below.

According to this invention, there is provided a stable, dry, antithrombin preparation containing antithrombin-III of human origin.

This invention also provides a dry antithrombin preparation containing antithrombin-III as a main ingredient and an effective quantity of at least one kind of stabilizer selected from the group consisting of proteins, sugars, amino acids, inorganic salts and salts of organic acids.

Further, according to this invention, there is provided a process for producing a dry antithrombin preparation characterized by freeze-drying an aqueous solution of antithrombin-III of human origin in the presence of an effective quantity of at least one kind of stabilizer selected from the group consisting of proteins, sugars, amino acids, inorganic salts and organic salts.

The antithrombin-III used in this invention may be any antithrombin-III which has been purified by any disclosed process to a purity of 30% or higher, and the antithrombin-III itself is not particularly limited.

The stabilizer used in the freeze-drying treatment of antithrombin-III should be physiologically acceptable one. Examples of said stabilizer include inorganic salts such as sodium chloride, potassium chloride, sodium phosphate, potassium phosphate, sodium hydrogen carbonate and the like; organic salts such as sodium citrate, potassium citrate, sodium acetate, potassium oxalate and the like; proteins such as albumin, globulin, fibrinogen, urokinase, plasminogen, gelatin and the like; sugars such as mannitol, glucose, saccharose, heparin and the like; and amino acids such as glycine, lysine and the like. These stabilizers are also have an action as the stabilizer in the inactivating heat-treatment of hepatitis virus, which may be contained in the antithrombin-III.

An effective quantity of each stabilizer can sufficiently be obtained by adding 0.1–5.0 parts by weight of the stabilizer to an aqueous solution containing 1 part by weight of antithrombin-III. Among the stabilizers shown above, proteins, sugars and amino acids can also serve as an excipient of preparation, so that their combined use with other stabilizer is favorable. When two or more kinds of stabilizers are used in mixture, the total quantity of the additives may be in the above-mentioned range.

In using these stabilizers, a specified quantity of them is dissolved into an aqueous solution of antithrombin-III having an appropriate concentration and an appropriate pH. Concentration of the resulting solution should be in the range of 0.1–3 times isotonic concentration, and preferably equal to the isotonic concentration. pH of the aqueous solution should be adjusted to 6.2–9.0, preferably to 7–8.

The aqueous solution containing antithrombin-III and the stabilizer is subjected to a heat-treatment (60°

C., 10 hours) for inactivating hepatitis virus or to sterilizing filtration or to both of them, if necessary, after which it is divided into portions according to the package unit so that one package contains 1,000-100,000 units of antithrombin-III. Then the divided solution is rapidly freeze-dried to give a powdery preparation.

The dry preparation of antithrombin-III thus obtained contains 0.1-5.0 parts by weight of stabilizer per 1 part by weight of antithrombin-III.

In applying the preparation of this invention to a patient having DIC or fibrinopenia, it is made into a solution containing about 1-10% W/V of antithrombin-III with distilled water for injection or, more preferably, into a solution having a physiologically isotonic salt concentration and then the solution is administered intravenously. Though the dose may be selected appropriately according to needs, the preparation is generally used according to package unit. The preparation of this invention does not lose its activity at all in the freeze-drying treatment and has so high a time-stability that it keeps entirely stable even after being stored at 37° C. for about 24 months. Therefore, it is quite valuable in the medical field as an antithrombin preparation containing antithrombin-III as a main ingredient.

The titres of antithrombin-III mentioned in the specification and claim have been determined by reacting a sample with thrombin at 23° C. for 5 minutes, measuring the prolongation of coagulation time caused by addition of fibrinogen to the reaction mixture, and calculating the titre therefrom with reference to a calibration curve previously prepared. At this time, the unit of antithrombin activity is so selected for convenience that an antithrombin activity of a supernatant obtainable by heat-treating a normal human plasma at 56° C. for 3 minutes and then defibrinating the reaction product is taken as 100 units/ml.

In the specification and claims, W/V % denotes the percentage of unit weight of solute per unit volume of aqueous solution.

This invention will be illustrated in more detail by way of the following examples and experimental examples.

BEST MODE FOR CARRYING OUT THE INVENTION

EXAMPLE 1

10 Kg of fraction IV-1 paste obtained by the Chon's cold alcohol fractionation method was suspended in 100 liters of physiological sodium chloride solution. 5 W/V % of barium sulfate was added to the suspension and the mixture was stirred at room temperature for 30 minutes, whereby the slight quantity of prothrombin present in the mixture was adsorbed onto the barium sulfate and removed. 13 W/V % of polyethylene glycol #4000 was added to the supernatant, the resulting precipitate was removed by centrifugation, an additional 30 W/V % of polyethylene glycol #4000 was added thereto, and the resulting precipitate was recovered by centrifugation. The precipitate was dissolved into about 20 liters of cold physiological sodium chloride solution and poured into a previously prepared column of heparin-Sephalose to have antithrombin-III adsorbed thereon. The column was washed with 0.4 M solution of sodium chloride to remove proteins as impurities, after which 2.0 M solution of sodium chloride was poured into the column and the eluate was collected as a fraction of antithrombin-III. The yield was $510 \times 10^4$ units, and the recovery rate was about 50% based on the starting material.

The aqueous solution of purified antithrombin-III thus obtained was dialyzed overnight against 0.5 W/V % of sodium citrate and 0.4 W/V % of sodium chloride to give a 1 W/V % aqueous solution of antithrombin-III. 1 W/V % of human albumin was added, the mixture was subjected to sterilizing filtration by means of a sterile Millipore filter, and the filtrate was divided into 50,000 unit portions and freeze-dried to give dry preparations.

The titre after freeze-drying was 50,000 units, indicating no titre loss due to freeze-drying. The preparation showed no drop of titre nor deterioration of solubility even after standing at 37° C. for 24 months, demonstrating its extreme stability. When this freeze-dried preparation was dissolved in distilled water for injection and an amount of the solution corresponding to 40,000 units/kg was administered to five heads of mice through the tail vein, no abnormality was observed throughout the subsequent 7 days. When the same solution as above was administered to house rabbits at a dose of 5,000 units/kg, no abnormal change of body temperature was observed throughout the subsequent 24 hours.

EXAMPLE 2

1 liter of normal human plasma was heat-treated at 56° C. for 3 minutes and the deposited fibrin was removed by centrifugation. The supernatant was mixed with 5 W/V % of barium sulfate and stirred for 1 hour, after which the barium sulfate was removed by centrifugation. The supernatant was subjected to an adsorption treatment with aluminum hydroxide according to the method of Monkhouse et al. and then it was eluted to give a semi-purified antithrombin-III. The eluate was poured into a column of DEAE-cellulose previously equilibrated with 0.02 M acetate buffer solution to have the antithrombin-III adsorbed on the column. The column was washed with the same buffer solution as above and then subjected to the concentration gradient elution method with 1 M of sodium chloride to recover a fraction having a high antithrobmin-III activity. Its yield was $2.3 \times 10^4$ units. Sodium citrate was added to the aqueous solution of antithrombin-III so that the concentration of sodium citrate came to 0.6 M and its pH was adjusted to 7.8, after which it was heat-treated at 60° C. for 10 hours for the purpose of inactivating hepatitis virus and subsequently dialyzed overnight against 0.9% solution of sodium chloride followed by the centrifugal separation, whereby a transparent solution was obtained.

This 1 W/V % aqueous solution of antithrombin-III was mixed with 2 W/V % of mannitol and 0.2 W/V % of sodium citrate, the mixture was diluted with a small quantity of cold distilled water so that the concentration of sodium chloride came to 0.5 W/V %, pH of the dilution was adjusted to 7.6 with 1 N sodium hydroxide, it was subjected to a sterilizing filtration by means of a sterile Millipore filter, and the filtrate was divided into 5,000 unit portions and freeze-dried to give dry preparations.

The preparation had a titre of 4950 units after the freeze-drying, indicating no observable loss of titre. It showed no change in solubility nor loss in titre even after standing at room temperature for 24 months or longer.

In the same manner as in Example 1, 10,000 units/kg was administered to mice and the animals were observed for 7 days. The animals showed no abnormality with a normal increase of body weight, demonstrating the safety of the preparation. The same solution as above was administered to house rabbits at a dose of 2,000 units/kg. No abnormality was observed throughout the subsequent 24 hours.

EXAMPLE 3

1 W/V % of glycine, 0.2 W/V % of sodium chloride and 1 W/V % of human albumin were added to the 1 W/V % aqueous solution of purified antithrombin-III obtained in Example 1. After pH of the mixture was adjusted to 7.2, it was subjected to sterilizing filtration by means of a sterile Millipore filter, divided into 50,000 portions and freeze-dried to give dry preparations. After drying, no loss in titre was observed and the solubility was kept good.

EXAMPLE 4

0.5 W/V % (5,000 units/ml) of urokinase (manufactured by Green Cross Corporation), 0.3 W/V % of sodium chloride and 1 W/V % of mannitol were added to the 1 W/V % aqueous solution of purified antithrombin-III obtained in Example 1. After pH of the mixture was adjusted to 7.2, it was subjected to sterilizing filtration by means of a sterile Millipore filter, divided into 50,000 unit portions and freeze-dried to give dry preparations. After drying, no loss in titre was observed and the solubility was kept good. The activity of antithrombin-III was stable even after standing at 37° C. for 24 months.

EXAMPLE 5

A dry preparation was obtained by repeating the procedure of Example 4, except that the urokinase was replaced by 0.1 W/V % of heparin. After drying, no loss in titre was observed and the solubility was kept good. The activity of antithrombin-III was stable even after standing at 37° C. for 24 months.

Experimental Example

Using an antithrombin-III which had been purified and recovered according to Example 1, time-stabilities brought about by addition of various stabilizers were experimentally compared. Thus, in this experiment, a liquid bulk of antithrombin-III was mixed with various stabilizers and freeze-dried and the residual activity rates just after the drying and after a lapse of one year were investigated, taking the activity before the drying as 100. The samples were prepared by adjusting 10 ml of an aqueous solution containing 50,000 units of antithrombin-III (0.5 W/V %) to pH 7.5-7.7 and adding various stabilizers thereto in the proportions mentioned in the following table. The results of the experiments are summarized in the following table.

TABLE

| Stabilizer and its proportion | Residual activity rate | | | |
|---|---|---|---|---|
| | Just after drying | After 3 months | After 6 months | After 12 months |
| Albumin (1%) | 100 | 100 | 100 | 100 |
| Albumin (1%) and sodium chloride (0.5%) | 108 | 103 | 100 | 100 |
| Sodium chloride (1%) | 101 | 101 | 102 | 101 |
| Albumin (1%) and Sodium citrate (0.4%) | 100 | 103 | 102 | 100 |
| Sodium citrate (1.0%) | 100 | 100 | 101 | 102 |
| Mannitol (1%) | 100 | 103 | 101 | 100 |
| Mannitol (1%) and Potassium oxalate (0.5%) | 100 | 100 | 101 | 101 |
| Gelatin (1%) | 101 | 101 | 102 | 102 |
| Lysine (1.5%) | 100 | 100 | 100 | 101 |
| Albumin (1%) and Sodium citrate (0.4%) and Sodium chloride (0.5%) | 102 | 103 | 103 | 102 |
| None | 67 | 60 | 0 | 0 |

We claim:

1. A freeze-dried antithrombin preparation containing an effective quantity of antithrombin-III and an effective quantity of at least one member selected from the group consisting of albumin, urokinase, gelatin, mannitol, heparin, glycine and lysine as stabilizer therefore.

2. A freeze-dried antithrombin preparation according to claim 1, wherein the quantity of said stabilizer is 0.1-5.0 parts by weight based on 1 part by weight of antithrombin-III.

3. A freeze-dried antithrombin preparation according to claim 1 wherein the antithrombin-III has been heat-treated for the purpose of inactivating hepatitis virus.

4. A freeze-dried antithrombin preparation according to claim 1, wherein there is employed at least one member selected from the group consisting of albumin, urokinase, and gelatin.

5. A freeze-dried antithrombin preparation according to claim 1, wherein there is employed at least one member selected from the group consisting of mannitol, and heparin.

6. A freeze-dried antithrombin preparation according to claim 1, wherein there is employed at least one member selected from the group consisting of glycine and lysine.

7. A freeze-dried antithrombin preparation according to claim 1 consisting essentially of antithrombin-III and said stabilizer.

8. A preparation according to claim 7 wherein the stabilizer is albumin.

9. A preparation according to claim 7 wherein the stabilizer is urokinase.

10. A preparation according to claim 7 wherein the stabilizer is gelatin.

11. A preparation according to claim 7 wherein the stabilizer is mannitol.

12. A preparation according to claim 7 wherein the stabilizer is heparin.

13. A preparation according to claim 7 wherein the stabilizer is glycine.

14. A preparation according to claim 7 wherein the stabilizer is lysine.

15. A process of remedying disseminated intravascular coagulation or fibrinopenia comprising administering to a patient suffering therefrom an effective amount of an aqueous solution of the antithrombin-III preparation of claim 1.

* * * * *